United States Patent [19]

Kristinsson

[11] Patent Number: 4,634,446
[45] Date of Patent: Jan. 6, 1987

[54] DEVICE FOR MOUNTING AN ARTIFICIAL LIMB TO THE STUMP OF AN AMPUTATED LIMB

[76] Inventor: Össur Kristinsson, Box 5288, 125 Reykjavik, Iceland

[21] Appl. No.: 234,149

[22] Filed: Feb. 13, 1981

[51] Int. Cl.[4] .......................... A61F 2/60; A61F 2/78; A61F 2/80
[52] U.S. Cl. ........................................ 623/33; 623/34
[58] Field of Search ........................................ 3/17–20, 3/2; 623/33–37, 27

[56] References Cited

U.S. PATENT DOCUMENTS

| | | | |
|---|---|---|---|
| 648,345 | 4/1900 | Peer | 3/17 R UX |
| 1,066,605 | 7/1913 | Hanger | 3/17 R |
| 1,497,219 | 6/1924 | Martino | 3/19 |
| 1,528,257 | 3/1925 | Mason | 3/19 |
| 2,273,695 | 2/1942 | Dew | 3/17 R |
| 2,669,728 | 2/1954 | Ritchie | 3/17 R |
| 2,696,011 | 12/1954 | Galdik | 3/17 SS |
| 2,808,593 | 10/1957 | Andersen | 3/17 SS |
| 2,947,307 | 8/1960 | Hoppe | 3/19 UX |

Primary Examiner—Ronald L. Frinks
Attorney, Agent, or Firm—Sughrue, Mion, Zinn, Macpeak & Seas

[57] ABSTRACT

A device for attaching an artificial limb to the stump of an amputated limb. The device comprises a sleeve (1, 2) intended for receiving the stump, the sleeve being in load-transferring connection with the artificial limb. The sleeve is made of a flexible material which is non-stretchable when subjected to the loads in question. The shape and volume of the sleeve are arranged to be adapted to the stump so as to obtain substantially total contact between the surface of the stump and the inner surface of the sleeve for distribution of the forces acting on the stump over the inner surface of the sleeve. For the purpose of transferring the load between the sleeve and the artificial limb a load-transferring construction (7, 8, 10) connected with the artificial limb is attached to the proximal end of the sleeve. Means (17) are also included for fixing the position of the distal end of the sleeve (1, 2) relative to the artificial limb.

1 Claim, 13 Drawing Figures

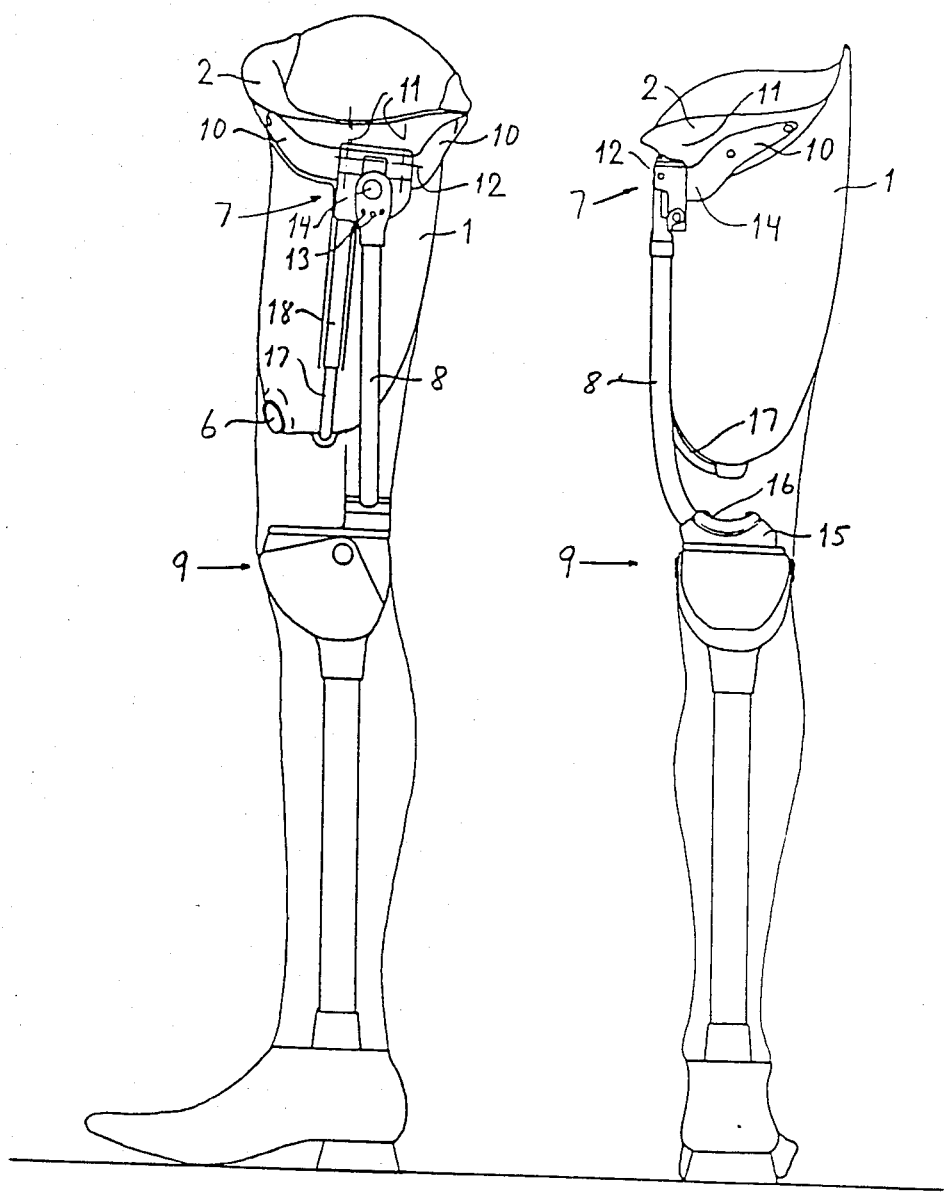

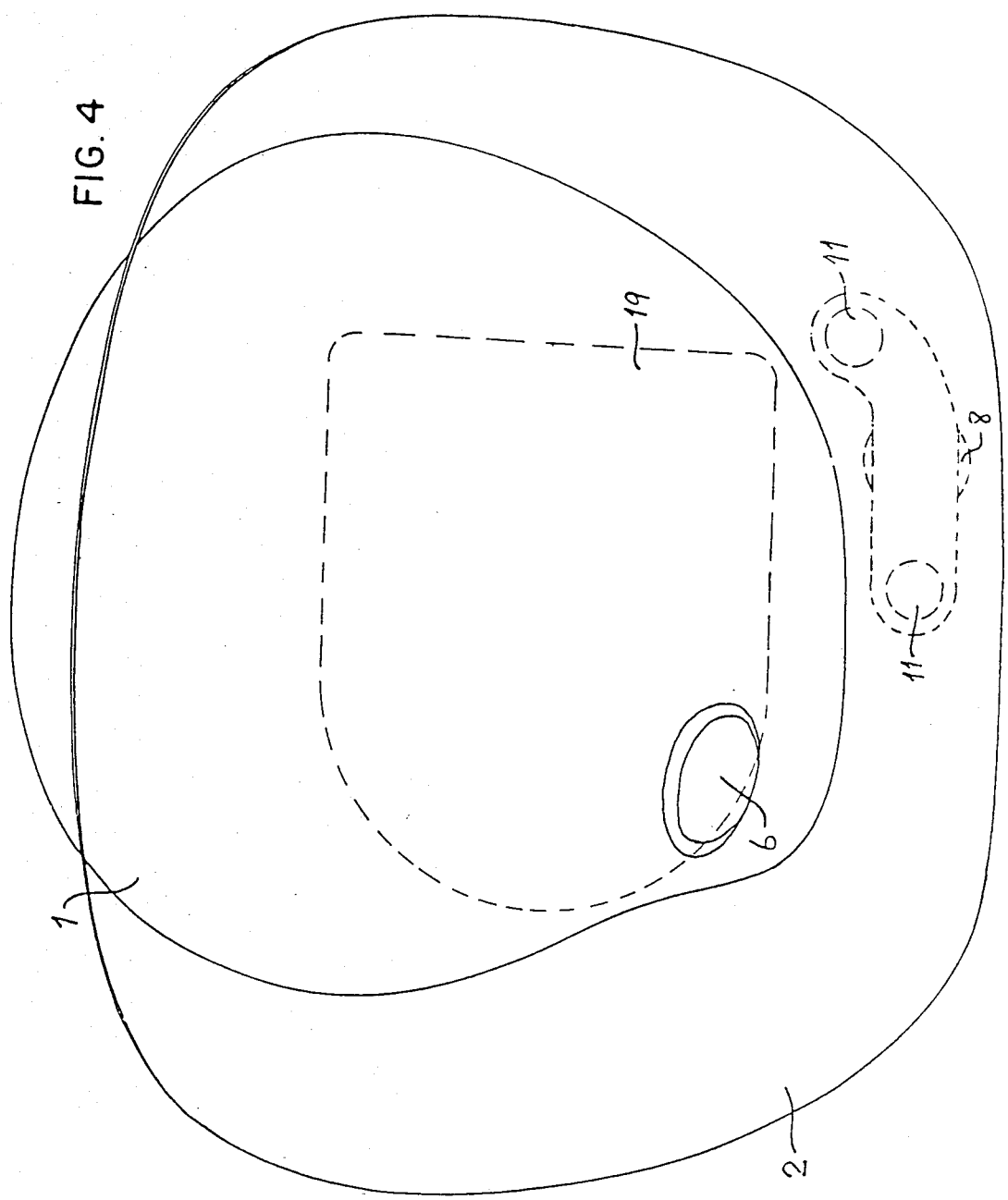

DEVICE FOR MOUNTING AN ARTIFICIAL LIMB TO THE STUMP OF AN AMPUTATED LIMB

The present invention relates to a device for attaching an artificial limb to the stump of an amputated limb, said device including a sleeve intended to receive the stump which sleeve is closed at one end and which is in force-transmitting connection with said artificial limb.

The most important part of an artificial limb which, for example, is to be fitted to the stump of a leg which has been amputated above the knee is the sleeve which connects the artificial limb, hereinafter referred to as the prosthesis, to the stump. It is of the greatest importance with respect of the comfort of the wearer of the prosthesis and the function of said prosthesis that the sleeve fits correctly and has exactly the right volume. In order to achieve this, the prosthesis sleeve must always be fitted individually. Standard sleeves at present on the market are not suited for prolonged use.

Despite the fact that new materials and methods of manufacture have been proposed for manufacturing the sleeve, the materials and methods used today are normally those which were used twenty years ago. Conventional prosthesis sleeves, which constitute part of the force-transmission system, are today normally manufactured from a plastics laminate, the model of the laminate constituting a gypsum positive which is a modified cast of the stump. The plaster positive is prepared by an orthopaedic technician from a negative, i.e. from a cast made directly on the stump. Different auxiliary means are available for stabilizing the soft part of the stump when taking the cast, to determine the sleeve volume required by the stump. Despite the auxiliary means at hand the final result when a stump is cast and the suitability of the sleeve prepared from said cast is greatly dependent on the expertise of the orthopaedic technician, and the precision with which the sleeve is made is normally relatively poor. Conventional methods of manufacturing a prosthesis sleeve are thus both time consuming and material consuming, since the precentage of rejects is relatively high. Furthermore, it is impossible to say definitely how well the finished sleeve will fit.

The known rigid sleeves used as load-transmitting elements also inhibit those changes in shape of the stump which continually take place as, for example, the wearer walks or those differences in shape which occur between a resting position and a working position. Thus, previously efforts have been concentrated on adapting a rigid system to a flexible body instead of attempting to find a solution which accepts the flexibility of the body and adapts itself thereto. The rigid inclusion of the stump can also cause a number of other problems, inter alia as a result of locally acting pressures.

In those cases when a soft or resilient sleeve has been used, said sleeve has only taken the form of an insert in a rigid, supporting sleeve which determines the conformity and stability of the system. If cavities have been made in the outer sleeve or an empty space has been left therein, this has only been for the purpose of easing the conditions of said locally acting pressures in order to free the soft inner sleeve from the determined contours of the hard outer sleeve, or to facilitate the insertion of the soft inner sleeve into the hard outer sleeve. Those soft inner sleeves which have been used for the aforementioned purpose have normally been manufactured from sponge rubber or a similar material, which means that the sleeves have been resilient and stretchable. No requirements have been placed on the dimension stability of the sleeve, since the rigid, outer sleeve has determined the shape.

The main object of the present invention is to provide a device of the kind mentioned in the introduction, in which the sleeve can be accurately adapted to the shape and volume of the stump of the amputated limb with the aid of simple means, and which sleeve is also able to permit continuous changes in the shape of the stump while the prosthesis is in use.

The aforementioned object is achieved in accordance with the invention by manufacturing the sleeve from a flexible material which is substantially unstretchable by those forces created when the prosthesis is in use; by arranging for the shape and volume of the sleeve to be adapted to the stump so that substantially total contact is obtained between the stump and the inner surface of the sleeve for distribution of the forces acting on the stump over the inner surface of the sleeve and by mounting a force-transferring structure connected to the prosthesis onto the sleeve at its inner or proximal, open end; and by arranging for the outer or distal, closed end of the sleeve to be fixed in position relative to the prosthesis.

By means of a device according to the foregoing it is possible to stably fix a prosthesis to the stump of an amputated limb without using a rigid sleeve which surrounds the stump. The flexible sleeve shall be accurately adapted to the volume and shape of the stump, so that substantially the same surface pressure is obtained over the whole surface of the stump. In this way, forces acting on the stump will be transferred, via said surface contact, to the flexible stump sleeve and to the prosthesis via the force-transmitting structure mounted on the proximal end of the sleeve. And by using a flexible sleeve in accordance with the invention the comfort afforded the wearer is very much increased since, inter alia, the sleeve can be readily made to exactly fit the shape of the stump. Preferably the sleeve is made in two parts, a slotted sleeve-shaped part and an element which is arranged to be inserted in said sleeve part and which has an extended portion which covers said slot, said element being referred to hereinafter as the brim. The extending part of the brim is suitably provided with an elongate flange which projects through the slot in the sleeve part, whereat both said flange and the edge parts of the slot are provided with holes through which, for example, a cord can be passed for lacing purposes.

Although the sleeve is preferably made of polyurethane it may also be made of a diagonally braided material, which further increases the comfort of the wearer.

In case of a device according to the above intended to be attached to a leg prosthesis whose proximal termination comprises an artificial knee or ankle joint, the force-transferring structure suitably comprises a holder means arranged to be attached to the proximal end of the sleeve and a bar structure which connects the holder means to a mounting means arranged to be attached to said knee joint or ankle joint. The device also includes means which enable the distal end of the sleeve to be fixed in a desired position relative to said joint.

The holder means suitably includes two arms which partially embrace the sleeve at its proximal end and which are either pivotable or flexible to permit the shape of the sleeve to adapt itself to changes in shape of the stump. The holder means is also preferably pivotable relative to said bar construction in at least two directions and the bar construction is attached to the artificial joint in a manner which permits the position of said bar construction to be adjusted. In this way optimal alignment of the sleeve relative to the prosthesis is possible on each separate occasion.

The invention will now be described in more detail with reference to the accompanying drawings.

FIGS. 3A and 3B illustrate a sleeve according to FIGS. 1 and 2 attached to a lower-leg prosthesis, seen from the inside and from the rear respectively.

FIG. 4 is a plan view of a sleeve attached in accordance with FIG. 3.

Figure 1A:
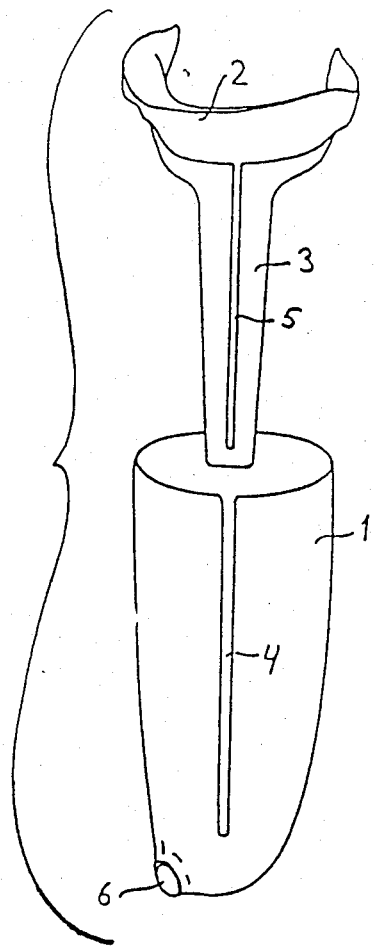
FIGS. 1A-1D and FIGS. 2A-2D illustrate a sleeve according to the invention intended for a thigh stump, in various different stages, seen from the inside and from the rear respectively.
Figure 2A:
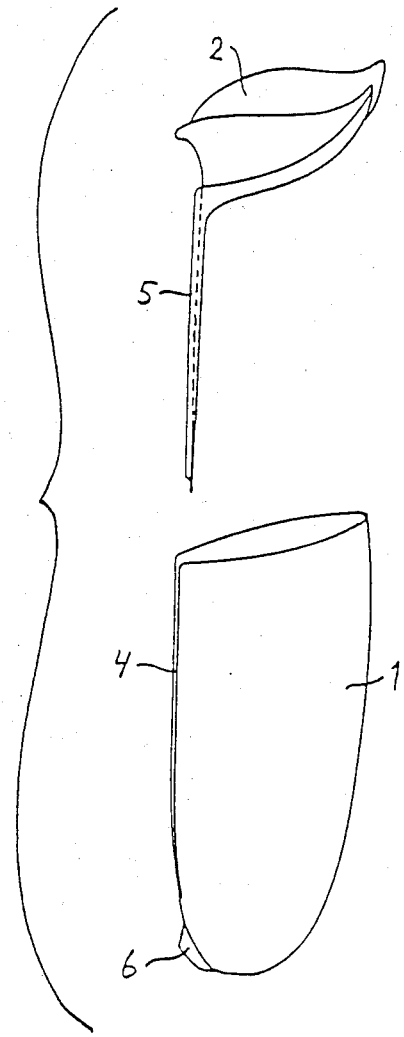

FIGS. 1A and 2A illustrate the starting blanks for a sleeve according to the invention, including a relatively long, sleeve-shaped part 1 and a brim 2 inserted into said sleeve-shaped part, said brim having an extended part 3. The sleeve 1 is provided with an elongate slit or slot 4 through which a flange 5 on the extended part 3 of the brim 2 is intended to project when the brim is inserted into the sleeve part 1. The reference 6 identifies a closeable opening through which a stocking used when placing the sleeve in position can be withdrawn.

The sleeve 1 is made of a flexible, but substantially non-stretchable material, such as polyurethane reinforced with woven glass fibres or nylon. The thickness of the material is suitable 2-3 mm. This makes the sleeve extremely flexible and enables the sleeve to conform to changes in the shape of the stump.

Figure 1B:
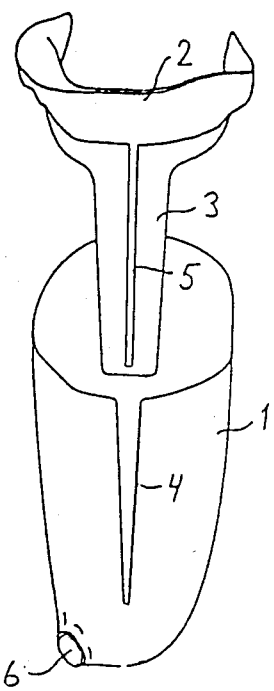
Figure 1C:
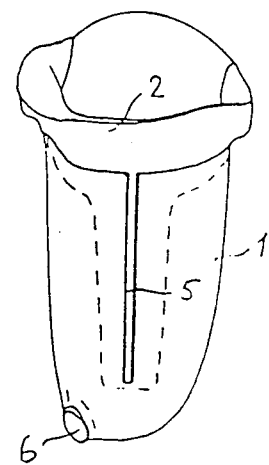
Figure 1D:
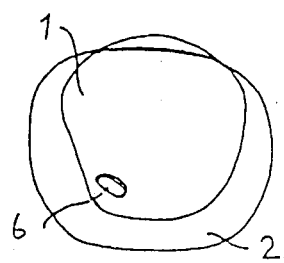
Figure 2B:
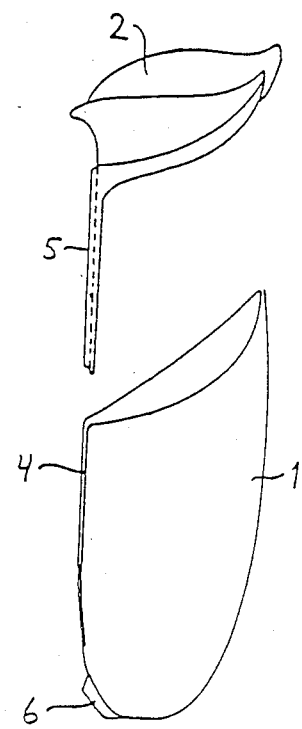
Figure 2C:
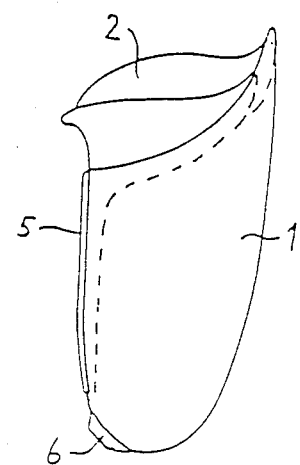
Figure 2D:
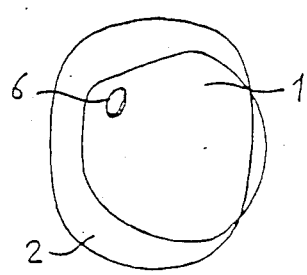

The blanks illustrated in FIGS. 1A and 2A can be readily adapted to the stump in question by decreasing or trimming the upper part of the sleeve 1 and by shaping said upper part and by correspondingly shortening the extended part 3 of the brim 2. In order to adapt the sleeve to stumps of smaller diameter, the slot 4 may also be enlarged, e.g., by removing wedge-shaped parts therefrom, which enables the sleeve to be drawn in. Thus, the sleeve 1 need only be manufactured in a few standard sizes. One sleeve 1 having a brim 2 and adjusted in the manner described above is illustrated in FIGS. 1B and 2B.

FIGS. 1C and 1D, and 2C and 2D respectively illustrate the sleeve 1 with the brim 2 completely inserted thereinto, whereat the flange 5 of the extended part 3 of the brim extends out through the slot 4. In the last mentioned figures, the sleeve 1 has been drawn together, for example by lacing, not shown, said laces passing through holes arranged in the edges of the slot 4 and in the flange 5. Such lacing enables the shape of the sleeve to be altered by the wearer whilst the prosthesis is in use. The brim and the sleeve, however, can also be fixed in position relative to one and other by riveting, sewing, glueing or like expedients.

Thus, when practicing the present invention it is possible by prefabricating sleeves in a few standard sizes to provide sleeves which can be made, in each case, to exactly fit the stump of the amputated limb. This is of great importance for the comfort of the wearer and also forms the basic requirement of the present invention, which is based on substantially total contact between the sleeve and the stump since it is endeavoured, in accordance with the invention, to achieve substantially the same compressive pressure over the whole surface of the stump. The flexibility of the sleeve enables the sleeve to conform to the varying shapes taken by the stump as a result of muscle activity. By particular design of the support collar at the upper edge of the sleeve it is also possible to achieve, in a known manner, ischium contact if so desired. The sleeve can be cut very easily with a knife and/or scissors. For the purpose of providing a tight sleeve an inner layer can be arranged on the wall of the sleeve on both sides of the slot 4, said layer enclosing the extended part 3 of the brim 2.

FIGS. 3A and 3B show the sleeve of FIGS. 1 and 2 mounted on a lower leg prosthesis. For this purpose there is used a holder means 7 which is connected to an artifical knee joint 9 via a supporting rod or bar 8. The holder means 7 is provided with two arms 10 which partially surround the sleeve and are fastened to the brim 2, which forms the upper edge part of the composite sleeve. The arms 10 are pivotable about substantially vertical axis 11, as is more clearly shown in FIG. 5, to enable the shape of the sleeve to adapt to changes in shape of the stump resulting from the varying loads acting thereon. The holder means 7 also permits the sleeve to be adjusted in a desired direction, by rotating the sleeve around an axis 12, whereat the sleeve may be set at a desired angle or inclination by means of setting screws 13. The sleeve may also be rotated about an axis 14 and, for example, locked by friction engagement between two serrated means.

Subsequent to moving the sleeve in the desired direction, by rotating the sleeve about the axis 12 and 14, it may be necessary to adjust the position of the prosthesis relative to the sleeve, so as to obtain the desired load line. For this purpose the rod 8 has at its lower end a curved portion which is received in a holder means 15 having a recess of corresponding radius. By causing the lower part of the rod 8 to move in the groove in the holder means 15, the sleeve will be displaced laterally relative to the prosthesis. Subsequent to obtaining the desired position of the sleeve, the rod 8 is firmly clamped in said position by means of a clamping means 16 arranged to cooperate with the holder means 15. The whole of the holder means 15 is also suitably arranged to be moved forwards and backwards relative to the prosthesis, this movement being guided by a dovetail groove. Alternatively the previous mentioned lateral displacement of the sleeve can also be guided in this manner.

As will be seen from the aforegoing, the sleeve 1 is only suspended at its upper edge portion. For the purpose of fixing the position of the distal end of the sleeve there is used in the illustrated embodiment a rod 17 which is mounted at said distal ends of the sleeve and which extends through a pocket 18 in the extended part 3 of the brim 2. As an alternative to the rod 17 there may be provided a simple, adjustable distance means between the rod 8 and the distal end of the sleeve. As will be understood, the rod 17 is not intended for the transfer of forces but merely to fix the position of the distal end of the sleeve.

FIG. 4 illustrates in plan view the combined sleeve and the prosthesis shown in FIG. 3, whereat the reference 19 identifies the support plate of the artificial knee joint 9. In other respects the reference numerals correspond to those used in the previous figures.

Figures 5A, 5B:
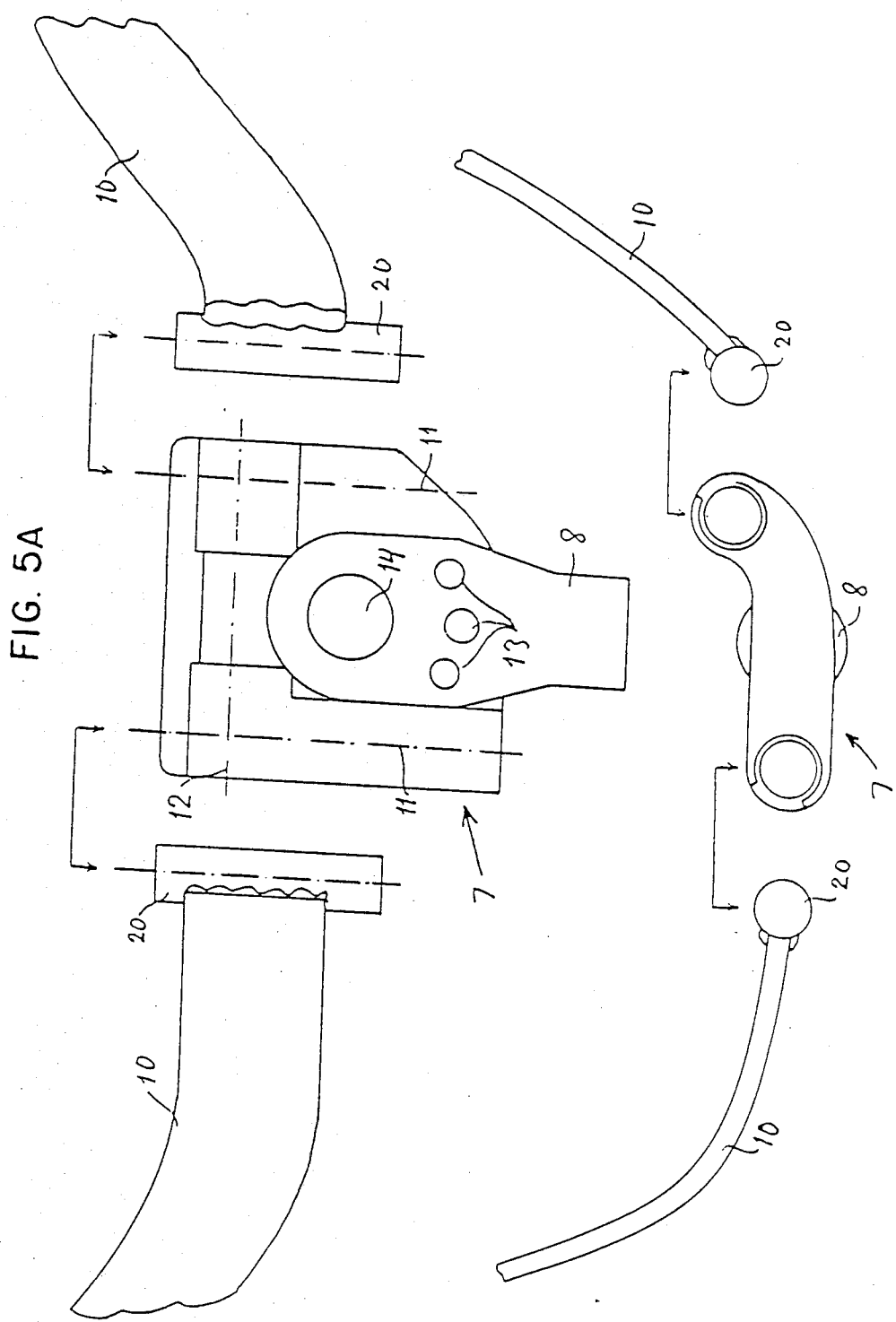
FIG. 5A and 5B illustrate some elements of the holder means for the sleeve according to FIG. 3, seen from the side and in plan respectively.

FIGS. 5A and 5B illustrate the holder means 7 from the side and in plan respectively. It will be seen from these figures that the arms 10 are provided with pivot pins 20 which are pivotably mounted in the holder means 7 and which permit the aforedescribed movement of the arms 10. The remaining reference numerals identify the same elements as those illustrated in previous figures.

The invention has been described above with reference to a thigh stump. It can be applied equally as well, however, with the stumps of a lower leg, upper arm and lower arm. In this respect, the material from which the sleeve is made can be selected as required, so as to achieve the flexibility sought for. Good flexibility is obtained, for example, when the sleeve is made from a diagonal woven material instead of a homogenous plastics material.

The invention can also be modified within the scope of the following claims. For example, both the holder means and the load-transferring connections between said holder means and the associated prosthesis can be varied as desired. A common feature of all embodiments, however, is that the flexible sleeve is suspended at its proximal end and that its distal end is fixed in the position desired.

What I claim is:

1. A device for mounting an artificial limb to the stump of an amputated limb, comprising a sleeve, intended to receive said stump, which sleeve is closed at one end and which is in force-transferring connection with said artificial limb, wherein the sleeve is made of a flexible material which is substantially nonstretchable under the loads or forces in question; the shape and volume of the sleeve are arranged to be adapted to the stump so as to obtain substantially total contact between the stump and the inner surface of the sleeve for distribution of the forces acting on the stump over the inner surface of the sleeve; the artificial limb is provided with a load-transferring structure which is attached to the sleeve at its inner or proximal, open end; the position of the outer distal, closed end of the sleeve is arranged to be fixed relative to the artificial limb; the sleeve has the form of a slotted, sleeve-like part and a brim arranged to be inserted into said sleeve-like part; the sleeve has an extended part which covers said slot; said extended part is provided an elongated flange which projects through the slot in the sleeve; and both said flange and the edge parts of the slot are provided with holes by means of which the sleeve can be laced.

* * * * *